United States Patent
Emani et al.

(10) Patent No.: US 10,478,290 B2
(45) Date of Patent: Nov. 19, 2019

(54) EXPANDABLE STENT VALVE

(71) Applicant: Children's Medical Center Corporation, Boston, MA (US)

(72) Inventors: Sitaram Emani, Newton, MA (US); James E. Lock, Chestnut Hill, MA (US); Pedro J. del Nido, Lexington, MA (US); Audrey C. Marshall, Milton, MA (US)

(73) Assignee: Children's Medical Center Corporation, Boston, MA (US)

( * ) Notice: Subject to any disclaimer, the term of this patent is extended or adjusted under 35 U.S.C. 154(b) by 145 days.

(21) Appl. No.: 15/039,510

(22) PCT Filed: Nov. 26, 2014

(86) PCT No.: PCT/US2014/067579
§ 371 (c)(1),
(2) Date: May 26, 2016

(87) PCT Pub. No.: WO2015/081175
PCT Pub. Date: Jun. 4, 2015

(65) Prior Publication Data
US 2017/0014228 A1  Jan. 19, 2017

Related U.S. Application Data

(60) Provisional application No. 61/909,124, filed on Nov. 26, 2013.

(51) Int. Cl.
*A61F 2/24* (2006.01)
*A61F 2/06* (2013.01)

(52) U.S. Cl.
CPC .......... *A61F 2/2418* (2013.01); *A61F 2/2409* (2013.01); *A61F 2002/061* (2013.01);
(Continued)

(58) Field of Classification Search
CPC .... A61F 2002/068; A61F 2/24; A61F 2/2418; A61F 2/07; A61F 2/82; A61F 2/90;
(Continued)

(56) References Cited

U.S. PATENT DOCUMENTS 4,692,164 A * 9/1987 Dzemeshkevich ... A61F 2/2412
623/2.14
5,606,928 A 3/1997 Religa et al.
(Continued)

FOREIGN PATENT DOCUMENTS

WO WO 2012/018779 A2 2/2012

OTHER PUBLICATIONS

Invitation to Pay Additional Fees dated Jan. 30, 2015 in corresponding International Application No. PCT/US2014/067579.
(Continued)

*Primary Examiner* — Seema Mathew
(74) *Attorney, Agent, or Firm* — Wolf, Greenfield & Sacks, P.C.

(57) ABSTRACT

An expandable valve (100) and valve frame device that may be implanted within the body, for example, at a position of the heart. The device may be surgically implanted and subsequently expanded at a later time. The device may include an expandable sewing member (160) surrounding the valve frame (130) at a region between upstream and downstream ends of the device, for attaching the device to surrounding tissue. The device may include a membrane (140) for blocking leakage out the side of the valve frame between opposite ends. However, the membrane may include a side opening (170) for guiding fluid flow toward an appropriate anatomical outflow tract. The device may include a hood-like covering attached to a tissue wall, for smoothly receiving and guiding fluid flow along a perpendicular bend. The device may further include a flared
(Continued)

opening at a downstream end, providing adequate space for device attachment.

15 Claims, 11 Drawing Sheets

(52) U.S. Cl.
CPC .............. *A61F 2220/0008* (2013.01); *A61F 2220/0075* (2013.01); *A61F 2230/0067* (2013.01); *A61F 2250/0039* (2013.01); *A61F 2250/0069* (2013.01)

(58) Field of Classification Search
CPC ........ A61F 2002/821; A61F 2220/0016; A61F 2/2412; A61F 2/954
See application file for complete search history.

(56) References Cited

U.S. PATENT DOCUMENTS

| | | | | |
|---|---|---|---|---|
| 6,030,414 A * | 2/2000 | Taheri | ............... | A61F 2/07 623/1.1 |
| 6,729,356 B1 * | 5/2004 | Baker | ............... | A61B 17/12022 139/383 AA |
| 2003/0204242 A1 * | 10/2003 | Zarins | ............... | A61F 2/07 623/1.16 |
| 2003/0236567 A1 * | 12/2003 | Elliot | ............... | A61F 2/07 623/1.13 |
| 2005/0131517 A1 * | 6/2005 | Hartley | ............... | A61F 2/07 623/1.13 |
| 2005/0171599 A1 * | 8/2005 | White | ............... | A61F 2/064 623/1.36 |
| 2007/0233229 A1 * | 10/2007 | Berra | ............... | A61F 2/07 623/1.13 |
| 2008/0114446 A1 * | 5/2008 | Hartley | ............... | A61F 2/07 623/1.13 |
| 2008/0140110 A1 * | 6/2008 | Spence | ............... | A61F 2/06 606/200 |
| 2008/0262594 A1 * | 10/2008 | Morris | ............... | A61F 2/07 623/1.13 |
| 2011/0098802 A1 | 4/2011 | Braido et al. | | |
| 2012/0101571 A1 | 4/2012 | Thambar et al. | | |
| 2012/0150274 A1 * | 6/2012 | Shalev | ............... | A61F 2/856 623/1.12 |
| 2012/0158121 A1 * | 6/2012 | Ivancev | ............... | A61F 2/06 623/1.13 |
| 2013/0103134 A1 * | 4/2013 | Minion | ............... | A61F 2/07 623/1.11 |
| 2013/0274873 A1 * | 10/2013 | Delaloye | ............... | A61F 2/2409 623/2.18 |
| 2014/0288480 A1 * | 9/2014 | Zimmerman | ............... | A61F 2/07 604/8 |
| 2014/0358223 A1 * | 12/2014 | Rafiee | ............... | A61F 2/2418 623/2.13 |
| 2015/0039083 A1 * | 2/2015 | Rafiee | ............... | A61F 2/2436 623/2.11 |
| 2016/0030165 A1 * | 2/2016 | Mitra | ............... | A61F 2/2409 623/2.42 |
| 2016/0120643 A1 * | 5/2016 | Kupumbati | ............... | A61F 2/2418 623/2.18 |
| 2016/0120667 A1 * | 5/2016 | Bolduc | ............... | A61F 2/856 623/1.14 |
| 2016/0194425 A1 * | 7/2016 | Mitra | ............... | A61F 2/07 623/1.11 |
| 2016/0199177 A1 * | 7/2016 | Spence | ............... | A61F 2/2409 623/2.38 |
| 2016/0338823 A1 * | 11/2016 | Akingba | ............... | A61F 2/07 |
| 2016/0354201 A1 * | 12/2016 | Keogh | ............... | A61F 2/2418 |
| 2016/0367359 A1 * | 12/2016 | Scorsin | ............... | A61F 2/2412 |

OTHER PUBLICATIONS

International Search Report and Written Opinion dated Mar. 31, 2015 in corresponding International Application No. PCT/US2014/067579.
International Preliminary Report on Patentability dated Jun. 9, 2016 in corresponding International Application No. PCT/US2014/067579.

* cited by examiner

EXPANDABLE STENT VALVE

This application is a National Stage under 35 U.S.C. § 371 of International Application No. PCT/US2014/067579, filed Nov. 26, 2014, which claims the benefit of U.S. Provisional Application No. 61/909,124, filed Nov. 26, 2013, the contents of both of which are incorporated herein by reference in their entireties.

BACKGROUND

1. Field

Aspects herein relate to expandable stent valve devices for tissue implantation and methods of use.

2. Discussion of Related Art

Natural heart valves are identified as the aortic, mitral, tricuspid and pulmonary valves.

The mitral valve is located between the left atrium and the left ventricle, and is commonly referred to as a bicuspid valve, having two cusps for allowing oxygenated blood to flow from the left atrium to the left ventricle. The tricuspid valve is located between the right atrium and the right ventricle, and has three cusps for allowing deoxygenated blood to flow from the right atrium to the right ventricle.

Aortic and pulmonary valves, commonly referred to as semilunar valves, are located at the base of the aorta and the pulmonary artery, respectively. Each semilunar valve has three cusps and permits blood to flow from the respective ventricular outflow tract into the appropriate artery, while preventing backflow of blood from the artery into the ventricle. The aortic valve lies between the left ventricular outflow tract (LVOT) and the aorta, and the pulmonary valve lies between the right ventricular outflow tract (RVOT) and the pulmonary artery.

Stenosis and regurgitation of the heart valves can cause chronic pressure within various chambers of the heart and volume loads leading to short term and long term morbidity, as well as mortality. A therapeutic option for patients that suffer from eventual heart failure is valve replacement. However, replacing a natural valve with a bioprosthesis has often led to progressive valve deterioration, despite administration of anticoagulation therapy.

Transcatheter valve replacement for adults is a strategy for mitigating problems associated with multiple surgical procedures and/or palliative medical care. Valve implants are designed to replace the leaflet structure that extends from a valve circumference to a radial center point of the valve, with each leaflet contacting or slightly overlapping the other adjacent leaflet(s). However, using current methods, transcatheter valve replacement is largely impossible for smaller patients, such as children.

SUMMARY

The inventors have improved upon existing implantable stent valve devices and their methods of use. For instance, the inventors have appreciated that it would be advantageous to surgically implant appropriately constructed stent valves into certain locations of the heart, and subsequently employ transcatheter methods, as needed (e.g., due to patient growth), to expand respective stent valves, while maintaining valve functionality, at the implanted location.

The inventors have devised of a number of structural features that provide certain advantages, when implemented with an implantable stent valve device. Methods and devices described herein are particularly suited for growing patients, such as children, where the dimensions of biological passageways alter with time.

In an illustrative embodiment, a device for implantation at a position of a heart is provided. The device includes a valve frame defining a lumen, the valve frame having an upstream end and a downstream end; a plurality of valve leaflets attached to and disposed within the valve frame; and a sewing member surrounding the valve frame at a region between the upstream end and the downstream end, for forming an attachment to tissue at the position of the heart. By surrounding the valve frame at a location between opposite ends, the sewing member may be particularly suited for forming an attachment of the device to surrounding tissue, for example, at a position of the heart (e.g., mitral valve position, transmural position).

In another illustrative embodiment, a method of implanting a device at a position of the heart is provided. The device including a valve frame defining a lumen, the valve frame having an upstream end and a downstream end, and a plurality of valve leaflets attached to and disposed within the valve frame. The method includes positioning the valve frame at the position of the heart; and attaching a sewing member surrounding the valve frame at a region between the upstream end and the downstream end to tissue at the position of the heart.

In yet another illustrative embodiment, a device for implantation at a position of a heart is provided. The device includes a valve frame defining a lumen, the valve frame having an upstream end and a downstream end; a membrane disposed about the valve frame for obstructing fluid flow between the lumen and an external region surrounding the valve frame, wherein a portion of the membrane at a side region and proximate the downstream end of the valve frame comprises an opening that permits fluid flow there through; and a plurality of valve leaflets attached to and disposed within the valve frame. The opening located at the side (e.g., circumferential region) of the membrane proximate the downstream end of the valve frame may be suitable to accommodate fluid flow from the lumen of the valve frame toward an appropriate vessel of the heart (e.g., left ventricular outflow tract, coronary artery).

In another illustrative embodiment, a device for implantation at a position of a heart is provided. The device includes a valve frame defining a lumen, the valve frame having an upstream end and a downstream end; a plurality of valve leaflets attached to and disposed within the valve frame; and a covering comprising a membrane, or other flexible material, attached to the valve frame at the upstream end, the covering having an opening that faces in a direction for receiving and guiding fluid, flowing near the upstream end substantially perpendicular to a longitudinal axis of the valve frame, into the lumen of the valve frame. The opening of the covering may be suitably sized and positioned so as to receive fluid flow from an appropriate chamber of the heart (e.g., right ventricle), and direct such flow through the lumen of the valve frame (e.g., through the right ventricular outflow tract or pulmonary artery).

In an illustrative embodiment, a device for implantation at a position of a heart is provided. The device includes a valve frame defining a lumen, the valve frame having an upstream end and a downstream end, the downstream end associated with a flared opening, for accommodating attachment to tissue at a vessel of the heart; and a plurality of valve leaflets attached to and disposed within the valve frame. In some embodiments, the flared opening provides sufficient space for the downstream end of the valve frame to be suitably attached to an appropriate region of the heart (e.g., right ventricular outflow tract, pulmonary artery). In some cases, the valve frame itself may be flared at the downstream end, or an additional component, such as a flared sewing cuff, may be provided at the end of the device, attached to the valve frame.

In another illustrative embodiment, a method of implanting a device at a position of the heart is provided. The device includes a valve frame defining a lumen, the valve frame having an upstream end and a downstream end, and a plurality of valve leaflets attached to and disposed within the valve frame. The method includes positioning the valve frame at the position of the heart; attaching the valve frame, at the downstream end, to tissue at a vessel of the heart; and attaching a covering comprising a membrane, attached to the valve frame at the upstream end, to tissue at a wall of the heart, the covering having an opening that faces in a direction for guiding fluid, flowing near the upstream end substantially perpendicular to a longitudinal axis of the valve frame, into the lumen of the valve frame.

Various embodiments of the present invention provide certain advantages. Not all embodiments of the invention share the same advantages and those that do may not share them under all circumstances. Various embodiments described may be used in combination and may provide additive benefits.

Further features and advantages of the present invention, as well as the structure of various embodiments of the present invention are described in detail below with reference to the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which.

DETAILED DESCRIPTION

The inventors have appreciated that existing stent valve devices are designed to be deployed using relatively non-invasive transcatheter implantation techniques within fully grown adults, where passageways are large enough for the entire device to travel there through during deployment. Yet, such devices are incapable of being deployed within children, or adults with significantly smaller passageways. Accordingly, the inventors have recognized that it would be advantageous to surgically implant a suitable stent valve device within certain regions of the heart, or other parts of the body, of a person with small passageways that would not otherwise permit transcatheter implantation of the device.

That is, through open-heart surgery, embodiments of a stent valve device in accordance with the present disclosure may be implanted at an appropriate location within the heart, for example, at a position of the heart (e.g., semilunar, mitral, tricuspid valve position, transmural). The stent valve device, including a number of components (e.g., valve, valve frame, sewing members, etc.) are expandable. Thus, upon suitable implantation, the device may be subsequently expanded, once or multiple times using transcatheter methods, to the appropriate size(s), while maintaining suitable function of the valve in its expanded state(s).

The expandable stent valve device may have certain features that provide advantages depending on where the expandable stent valve device is deployed. Such features may be particularly suited, for example, to accommodate flow from a particular chamber of the heart through the lumen of the device, so that the patient is able to regain acceptable heart function. Or, such features may allow for the device to be suitably attached to tissue at an appropriate location of the heart, for example, at a particular valve position, an outflow tract or an artery (e.g., pulmonary, aortic).

Figure 1:
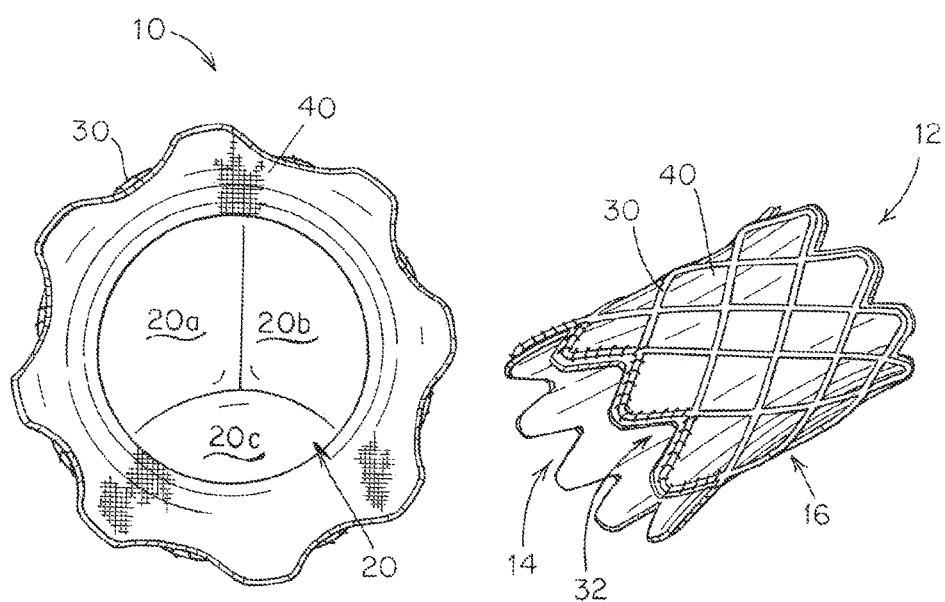
FIG. 1 shows a conventional valve having a frame surrounding the valve.

FIG. 1 depicts a conventional stent valve device 10 (e.g., MELODY® Valve) having a valve 20 and a valve frame 30. The valve frame 30 may be a stent that defines an internal lumen 32 within which valve leaflets 20a, 20b, and 20c are disposed.

The valve frame includes an upstream end 12 and a downstream end 14, located opposite one another. The upstream end 12 may also be referred to as the proximal end, where fluid flows into the lumen of the device, and the downstream end 14 may be referred to as the distal end, where fluid flows out of the lumen of the device. As shown in FIG. 1, both the upstream and downstream ends have crowns, illustrated to have a relatively jagged surface. Such a surface may allow for tissue ingrowth and attachment of the device to the surrounding tissue.

A membrane 40 is provided with the valve frame 30, surrounding the lumen and obstructing flow between the lumen and the exterior of the device, through a side region 16 of the device. Accordingly, flow through the lumen 32 is limited to entry and exit through the upstream and downstream ends only.

Each of the valve leaflets may be attached to the valve frame 30 and/or the membrane 40. During a single transcatheter procedure, the stent valve device 10 may be deployed and expanded via a balloon.

Examples of expandable valves, frames and methods of their use are disclosed in International Application No. PCT/US2011/046216 (International Publication No. WO 2012/018779), which is hereby incorporated by reference herein for details regarding the construction and use of an expandable stent valve device, its use and implementation.

FIGS. 2A-2D depict illustrative embodiments of an expandable stent valve device 100 in accordance with aspects of the present disclosure. The expandable stent valve device 100 includes a valve 120 attached to a valve frame 130. The valve frame 130 may be a stent that defines an internal lumen 132 within which the leaflets of the valve 120 are disposed. As shown, the valve frame has an upstream end 102 (proximal end) and a downstream end 104 (distal end), located opposite one another. The upstream end 102 may be the end of the valve frame through which fluid flows into the lumen, when implanted, as depicted by three solid arrows labeled "inflow." The downstream end 104 may be the opposite end of the valve frame through which fluid flows out from the lumen, when implanted, as depicted by three solid arrows labeled "outflow."

Each of the components of the device 100 may be expandable. It can be appreciated that when the components are suitably expanded, the device maintains its valve function. For example, the valve frame 130 may essentially be a stent that is expandable using methods known in the art, such as transcatheter balloon dilation. The valve 120 may also be expandable along with the valve frame 130. It can be appreciated that other components of the device (e.g., membrane, sewing member, etc.) may be expandable along with the valve frame and valve.

Figure 2A:
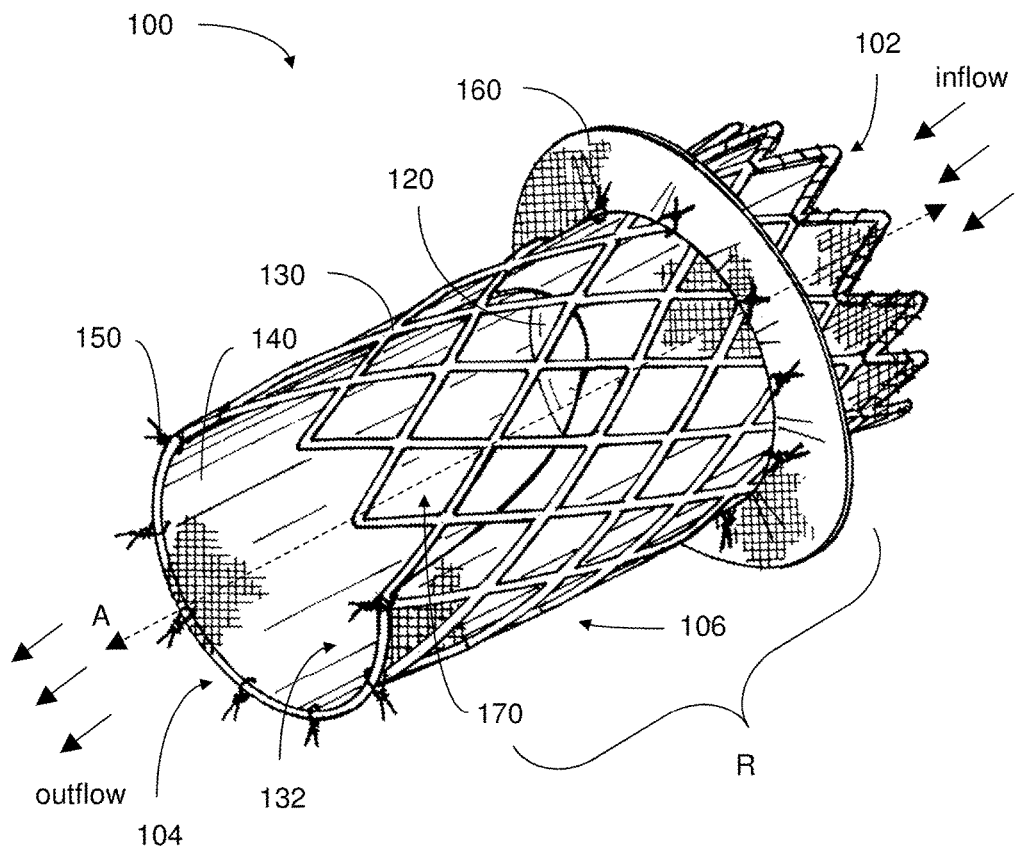
FIG. 2A depicts a perspective view of an implantable device in accordance with some embodiments.
Figure 2B:
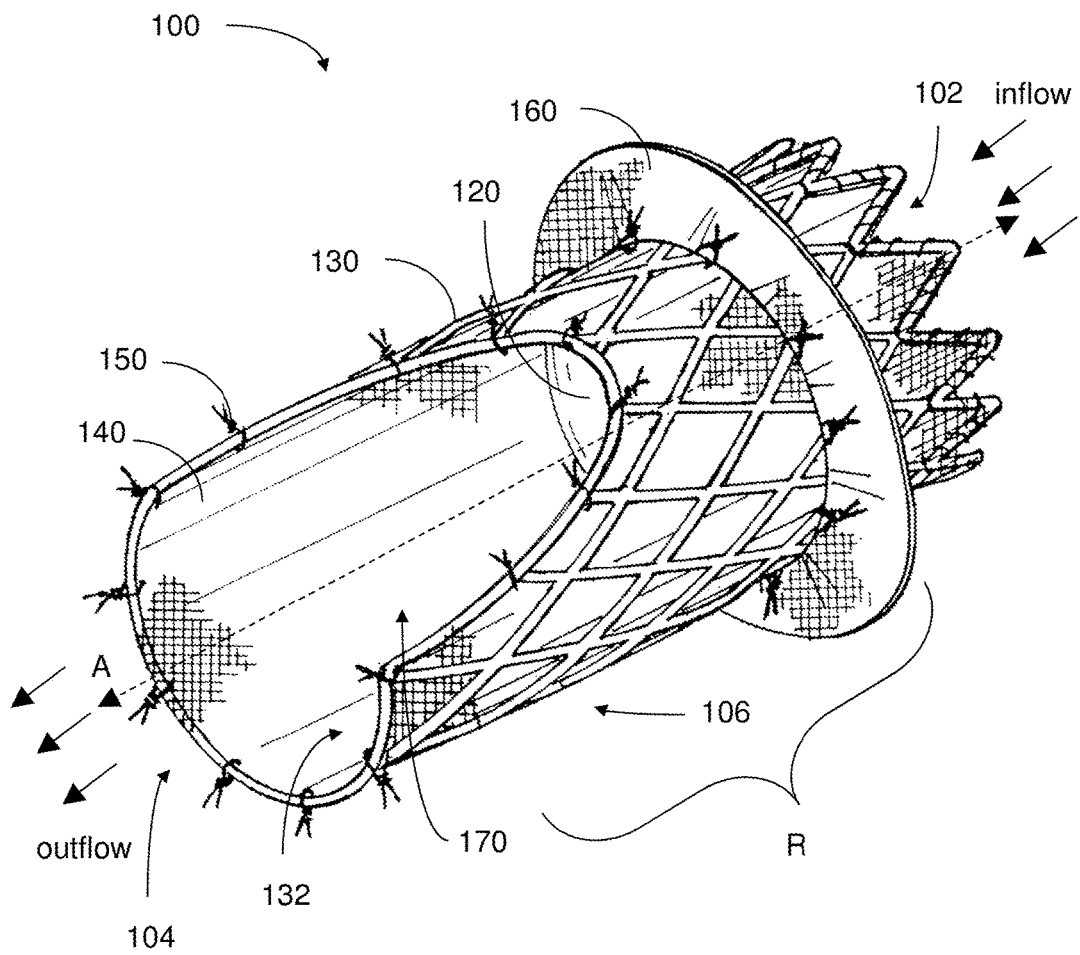
FIG. 2B depicts a perspective view of another implantable device in accordance with some embodiments.

In some embodiments, as shown in FIGS. 2A-2B, one, both or neither of the ends may have a crown that exhibits a jagged surface. For example, the upstream end 102 of the valve frame has a crown that has a jagged structure, similar to that shown above for both ends in the device of FIG. 1. Though, the downstream end 104 of the valve frame has no such crown, giving rise to a relatively even or smooth surface. That is, rather than exhibiting a zig-zag structure with peaks and valleys, such as that provided at the upstream end 102, the rim of the downstream end 104 exhibits a substantially level arcuate surface (e.g., at least partially circular or elliptical). Or, put another way, the downstream end 104 of the valve frame may have a shape that resembles a cross-sectional cut out that extends along a plane that is substantially perpendicular to the longitudinal axis A of the valve frame. It can be appreciated that one or both ends of the valve frame may exhibit a jagged (e.g., zig-zag) structure or a substantially even curved surface, as desired. For example, one end of the valve frame may have a jagged structure and the other end of the valve frame may have a substantially even curved surface. Or, both ends of the valve frame may have jagged structure, or a substantially even curved surface. Alternatively, either end of the valve frame may have a surface that exhibits a different shape altogether.

When the end(s) of the device exhibits a relatively level surface, during implantation or expansion of the valve frame, there may be a reduced risk that respective end(s) of the device snags or otherwise catches on to surrounding tissue in an undesirable manner. In some cases, when the valve frame has jagged crown ends, similar to the device illustrated in FIG. 1, it may be preferable for one or both ends to be appropriately cut or trimmed so that the rim of the cut end is substantially level (not jagged).

An appropriate biocompatible material suitable for use in a heart valve may surround, impregnate or otherwise be included with the valve frame, but is not shown for the purposes of clarity. In one embodiment, however, the material is stretchable so as to accommodate expanding dimensions (e.g., diameters) of various components of the device, including the valve frame, valve, sewing member, etc.

The valve frame may include any suitable material. In some embodiments, the valve frame is made up of a rigid material. In some embodiments, the valve frame is composed of a material that permits the frame to be expandable to one or more discrete sizes (e.g., frame diameters). The frame may be made from metal (e.g., stainless steel, alloys of suitable metals, etc.), shape memory material (e.g., nitinol), polymer (e.g., synthetic and/or naturally occurring), silicon, rubber, tissue (e.g., allograft and/or xenograft), and/or combinations thereof.

An optional membrane 140 or other suitable flexible material that may be expanded along with the valve frame may be attached or otherwise integrated with the valve frame 130 so as to guide fluid flow through the lumen. The membrane may serve to obstruct fluid flow between the internal lumen and the exterior of the device. That is, inclusion of the membrane may substantially prevent leakage out from the interior of the device.

It can be appreciated that, for some embodiments, the expandable stent valve device 100 does not include a membrane. For example, the device may include an expandable valve disposed within an expandable valve frame where fluid is permitted to flow, or leak, between the lumen of the device and external regions surrounding device, through spaces located between struts of the stent scaffolding.

The membrane may include any suitable material. As described herein, such a material may cover the valve frame so as to prevent or otherwise obstruct leakage of fluid from the device. The membrane may include one or more compositions, such as ePTFE (e.g., GORE-TEX®), biological materials (e.g., bovine tissue, porcine tissue, human tissue, etc.), synthetic materials (e.g., polyester, polyimide, PET, etc.) or other biocompatible materials. In some embodiments, the membrane may include an anisotropic material having an orientation that provides for the device to be expanded in a desired manner (e.g., direction and degree of expansion). For example, a membrane that includes an anisotropic material prone to expansion in one direction may be constructed so that the anisotropic material expands more readily, for example, in a radial direction as compared to a longitudinal direction, or vice versa. As such, the direction and degree of expansion of the device may be controlled through appropriate use and orientation of suitable materials. The membrane may include expandable PTFE, or any other appropriate biocompatible, generally compliant and thin material. Further, the membrane may include engineered biomaterials, such as for example a collagen scaffold.

Figure 2C:
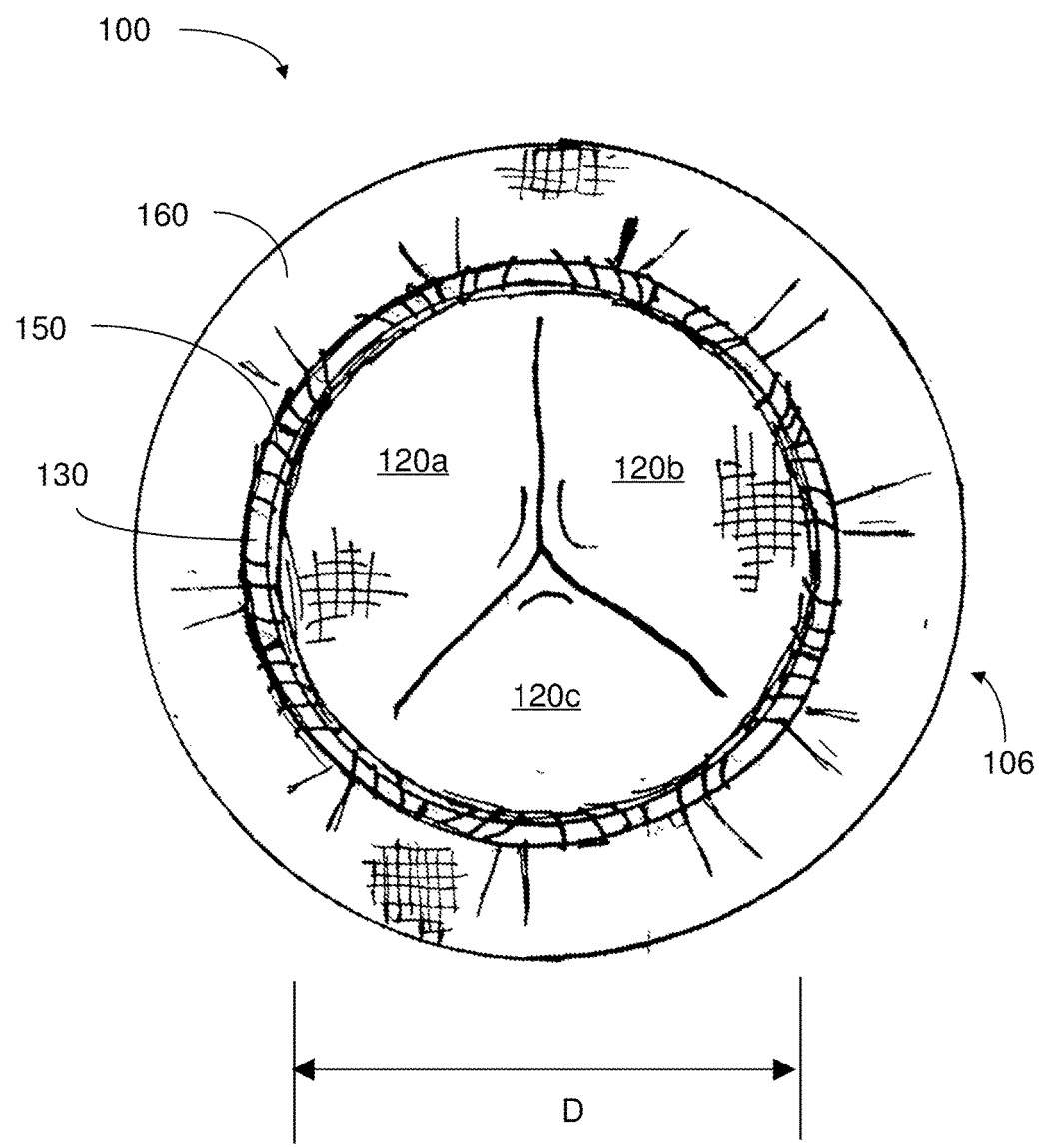
FIG. 2C illustrates a plan view from an end of an implantable device in accordance with some embodiments.
Figure 2D:
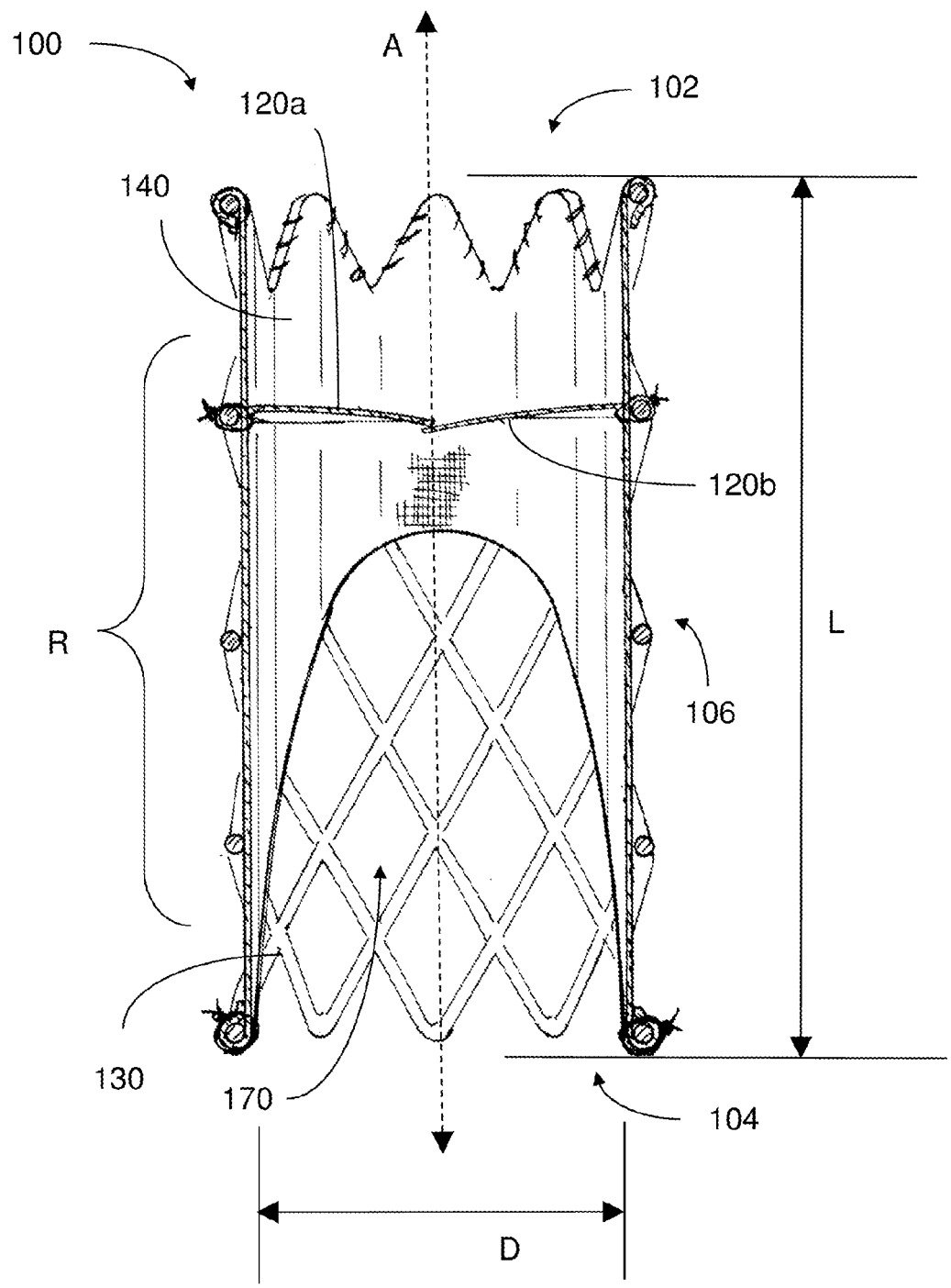
FIG. 2D shows a top plan view of an implantable device in accordance with some embodiments.

FIG. 2C depicts an embodiment of the device viewed from one of the ends, upstream or downstream, through the lumen, where the valve leaflets 120a, 120b, 120c are in a closed position and fluid is obstructed from passage there through. Of course, when the valve is in an open position (not shown), fluid is able to flow through the lumen and past the valve.

In some embodiments, the valve leaflets include material that is separate from the valve frame and/or the membrane. For example, the valve frame 130 and the valve 120 may be appropriately attached to one another where each of the valve leaflets are adhered or attached to the scaffolding structure provided by the valve frame 30 and/or the membrane 40. The valve leaflets may be attached to the membrane and/or the valve frame in any suitable manner, such as through a suture, fastener, adhesive, etc. For instance, the valve frame and the valve leaflets may be sutured or adhered together. An interlocking mechanism may serve to attach the valve frame and the valve leaflets to one another. As an example, the valve frame 130 and the valve leaflets 120 may include a complementary flanged arrangement that allows for the valve frame 130 and the valve leaflets 120 to be appropriately attached. In some embodiments, the valve frame may be surgically implanted within the heart simultaneously with the valve leaflets.

In some embodiments, the valve frame 130 and the valve leaflets 120 are formed as a monolithic, contiguous material. Or, each of the valve leaflets may be an extension of the membrane. For example, the valve and the membrane may also be provided as a contiguous material.

The valve, or portions of the valve, may include any suitable material. The valve or portions of a valve (e.g., valve leaflets) for implantation at a suitable position within the body may include, for example, a polymer (e.g., synthetic and/or naturally occurring), biological tissue (e.g., allograft and/or xenograft), and/or combinations thereof. The valve, or portions thereof, may include bovine tissue, porcine tissue, human tissue, or any other biological material (s). For example, suitable valves that may be incorporated within devices described herein may include valves harvested from human, bovine or porcine sources, such as the femoral vein of a human, valves produced by CryoLife, LifeNet, or another appropriate source. Or, for some embodiments, valve leaflets may be bioprosthetic valve leaflets and/or completely artificial valve leaflets.

It can be appreciated that the valve may be structured and formed of a material that allows for the valve to expand along with the valve frame.

As illustratively shown, the device may further include a sewing member 160 that surrounds the valve frame 130 at a suitable region R between the upstream end 102 and the downstream end 104. It can be appreciated that the sewing member may surround and be attached to the valve frame at any suitable location between the upstream and downstream ends. In some embodiments, the sewing member is attached to the valve frame at approximately the midpoint, or an appropriate distance offset from the midpoint, between opposite ends. For example, FIGS. 2A-2B illustrate the sewing member to be attached to the valve frame closer to the upstream end 102 than the downstream end 104. Alternatively, the sewing member may be attached to the valve frame at a position closer to the downstream end 104 than the upstream end 102 (not expressly shown in the FIGS. 2A-2B).

The sewing member 160 may have an appropriate composition and structure for forming an attachment between the device 100 and tissue, allowing the device to expand while attached to the surrounding tissue, without risk of perivalvular leakage.

As described herein, for some embodiments, the sewing member may be particularly suited to fix the device to tissue at a position of the heart (e.g., mitral/tricuspid valve position). For example, the device may be surgically inserted into a region of the heart where the anatomical valve leaflets have been partially or completely resected. In some embodiments, the sewing member provides a flanged arrangement for the device to be sutured, adhered or otherwise attached to the surrounding tissue of the valve annulus.

In some embodiments, the sewing member 160 is positioned to be substantially concentric with the valve of the device. Accordingly, when the sewing member 160 is fixed to the anatomical location where the biological valves were once situated, the valve leaflets of the device provide for a suitable valve replacement at the same location.

In some embodiments, the sewing member is a ring or cuff that is attached to and surrounds the periphery of the valve frame. The sewing member may also surround and be attached to the optional membrane which, when present, obstructs leakage of fluid flow from the lumen of the valve frame. In some cases, the sewing member may be attached to the valve frame and/or membrane by application of an adhesive (e.g., glue), pressure/heat sealing and/or by suturing directly to the valve frame itself. In some embodiments, the sewing member forms an annulus that surrounds and is fixed to the valve frame and/or membrane. In some embodiments, the sewing member may be employed so as to prevent or largely eliminate perivalvular leakage, or other such leakage of blood between atria and ventricles.

In some cases, the sewing member is pre-manufactured with the valve frame and/or membrane. Although, in other cases, the sewing member may be attached to the valve frame and/or membrane during device implantation.

The sewing member may be formed of any suitable material. For example, the sewing member may include ePTFE (e.g., GORE-TEX®), biological materials (e.g., pericardium, allografts, xenografts, etc.), synthetic materials (e.g., polyester, polyimide, polyethylene terephthalate, DACRON®, etc.), cloth-like material, or other biocompatible materials. The sewing member may comprise a material and/or structure that allows for expandability and may exhibit, for example, elasticity, corrugations, pleats, etc., as may be appreciated by those of skill in the art. As noted above, the sewing member 160 may be expandable, along with the valve frame, the membrane and the valve disposed within the valve frame.

It may be desirable for the properties of a sewing member to be similar or compatible with the region of tissue to which the sewing member is implanted or otherwise fixed, so as to form a suitable attachment. Accordingly, the sewing member may be selected to have characteristics and/or materials based on the properties of the tissue region where the respective sewing member will be attached. For example, the stiffness, elasticity, etc. of the sewing member may be chosen to match, as best possible, the corresponding stiffness, elasticity, etc. of the tissue at the region of implantation.

As shown in FIGS. 2A-2B, the device may include an opening 170 located at a side (or circumferential) region 106 of the device, proximate the downstream end 104 of the valve frame, that permits fluid flow there through. For instance, where conventional stent valves might include membranes that cylindrically surrounding the internal lumen from end to end, some embodiments of the present disclosure include an opening 170 that allows fluid to flow in and out through the side 106 of the device. In other words, fluid flowing into the upstream end 102 of the device may leak out the side opening 170, in the direction provided by the opening, rather than flowing completely through the lumen and out the downstream end 104. Accordingly, such an opening may be appropriate to accommodate fluid flow entering from the upstream end 102 of the frame so as to exit through both the downstream end 104 and the side opening 170, in an appropriate manner, and be directed toward a nearby vessel. The nearby vessel may be, for example, the left ventricular outflow tract for flow into the aorta or, for example, a coronary vessel for flow into the coronary arteries.

In some embodiments, the opening 170 is substantially shaped as a scalloped cut out of the valve frame 130 and/or membrane 104 that extends along a plane that is parallel to or forms an angle with respect to the longitudinal axis A of the valve frame. Such an angle may, for example, be between 0 degrees and 90 degrees, between 60 degrees and 90 degrees, between 10 degrees and 80 degrees, between 20 degrees and 70 degrees, or between 30 degrees and 60 degrees, with respect to the longitudinal axis A of the valve frame. Such an opening may conform to any appropriate slice through the valve frame and/or membrane.

In some embodiments, as shown in FIG. 2A, the device includes a membrane 140 having an opening 170 at the circumferential side region 106. As further shown, the scaffolding provided by the valve frame 130 remains intact, so as to provide structural support for the device upon implantation, while also permitting fluid flow through the opening 170. In some embodiments, as depicted in FIG. 2B, corresponding portions of both the valve frame 130 and the membrane 140 are removed so as to result in a clear opening 170 at the circumferential side 106 of the device proximate the downstream end 104, absent scaffolding struts or flexible membrane material.

Figure 3:
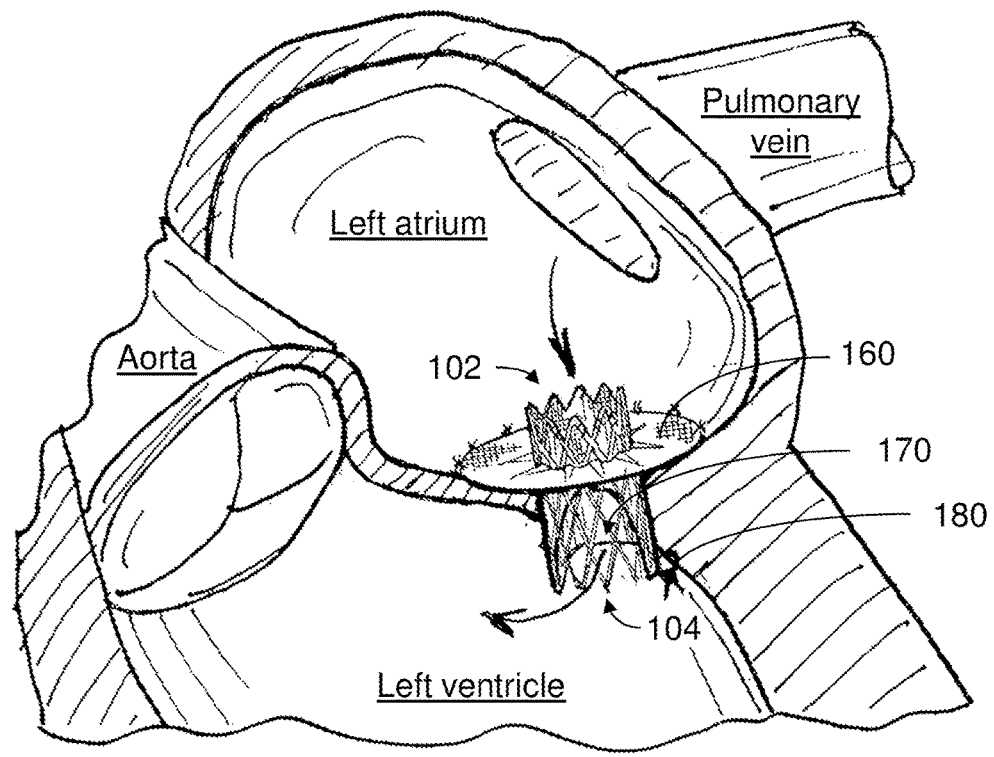
FIG. 3 shows an implantable device deployed within a heart in accordance with some embodiments.

FIG. 3 depicts an illustrative embodiment of a device 100 deployed within the heart at the mitral valve position, between the left atrium and the left ventricle. Here, the anatomical mitral valve leaflets are resected from the patient so as to make room for the device to be attached to the annulus of the surrounding tissue wall. As shown, the sewing member 160, surrounding and attached to the valve frame, is firmly sutured to the tissue wall, resulting in firm fixation of the device in place. Such an attachment may serve to reduce or otherwise eliminate perivalvular leakage while also allowing for the device to expand, for example, as the patient grows.

In some embodiments, multiple points of attachment are provided along the length of the device between the device and the surrounding tissue. For example, as shown in FIG. 3, in addition to being attached at the mitral valve location, the device may be further attached to the wall of the ventricle at a region 180, proximate the downstream end 104. The device may be attached to the heart at other locations as well.

In some cases, the downstream end of the device is anchored to the ventricular wall on a side of the device opposite to the opening 170. That is, the attachment point of the device to the tissue wall is approximately 180 degrees from the central region of the circumferential side opening 170. Accordingly, the device may be attached to the heart at multiple points along the length of the device; at the same time, the opening 170 may also be arranged so as to allow for fluid flow out the side 106 of the valve frame, accommodating fluid flow from the lumen toward the left ventricular outflow tract, and ultimately passing through the aortic valve.

While not a requirement for various embodiments of the present disclosure, by having multiple points of attachment at various locations along its length, the device may be firmly situated upon implantation. Otherwise, in some cases, attaching the device solely at the mitral valve position, without anchoring the device at one or more other locations, may give rise to a rocking or see-saw motion of the device and, thus, instability.

Though, it can be appreciated that the above-described rocking motion may also be mitigated by other methods, for example, by employing a shorter valve frame, which is less prone to such movement of the upstream and downstream ends about the point(s) of attachment. For instance, the longer the valve frame, the greater the potential for undesirable torque to be generated (e.g., by fluid flow, sudden muscle movement(s), etc.), giving rise to instabilities arising from the rocking motion. Though, when the valve frame is shorter (e.g., less than 2.5 cm, less than 2.0 cm in length), the potential for opposing ends of the device to exhibit a see-saw motion about the point(s) of attachment is reduced.

The valve frame may have any suitable length L. In some embodiments, the valve frame has a length of between 1.0 cm and 3.0 cm, between 1.0 cm and 2.5 cm, between 1.5 cm and 2.0 cm, or any other suitable length. In an example, during a surgical implantation, the original length of the valve frame was approximately 2.5 cm, and the length of the valve frame was trimmed to between 1.5-2.0 cm, so as to complement patient anatomy at the mitral valve location.

FIG. 3 further depicts arrows that illustrate the net direction of fluid flow through the heart. That is, oxygenated blood flows from the pulmonary vein and into the left atrium. The blood then flows into the implanted device (fixed at the mitral valve position) through the upstream end 102, passes through the valve, and then flows out the opening 170 toward the left ventricular outflow tract, which in turn leads to the aorta.

As discussed above, the opening 170 is provided at the side of the valve frame so as to accommodate fluid flow toward the ventricular outflow tract. Otherwise, in some cases, absent a suitable (side) opening, the blood may be directed toward the bottom end of the ventricle and collect in such a manner so as to require a greater amount of effort than is desired from the cardiac muscles to pump the blood through the ventricular outflow tract and through the aorta.

As described herein, upon implantation at a suitable position within the body (e.g., at a valve position of the heart, transmural position), the device, including the valve frame, the membrane, the valves, the sewing member and other components of the device, may be expandable to an appropriate size. For instance, the diameter of the expandable valve frame may be suitably increased when a sufficient outward force is applied to the frame (e.g., from a transcatheter balloon). Upon expansion of the valve frame, valve leaflets disposed within the valve frame may also be expanded (e.g., stretched, enlarged) along with the frame so that the diameter of the entire stent valve device is increased. The membrane, integrated with the valve frame for containing fluid flow within the lumen, may also be stretched or otherwise expanded with the valve frame.

When an expandable device in accordance with embodiments described herein is implanted in a young patient, the expandable valve frame, and associated valve and membrane, may be appropriately expanded to accommodate growth in the patient. In some embodiments, and as discussed further below, the diameter of an expandable valve frame may be increased through use of a dilation balloon catheter.

Figure 4A:
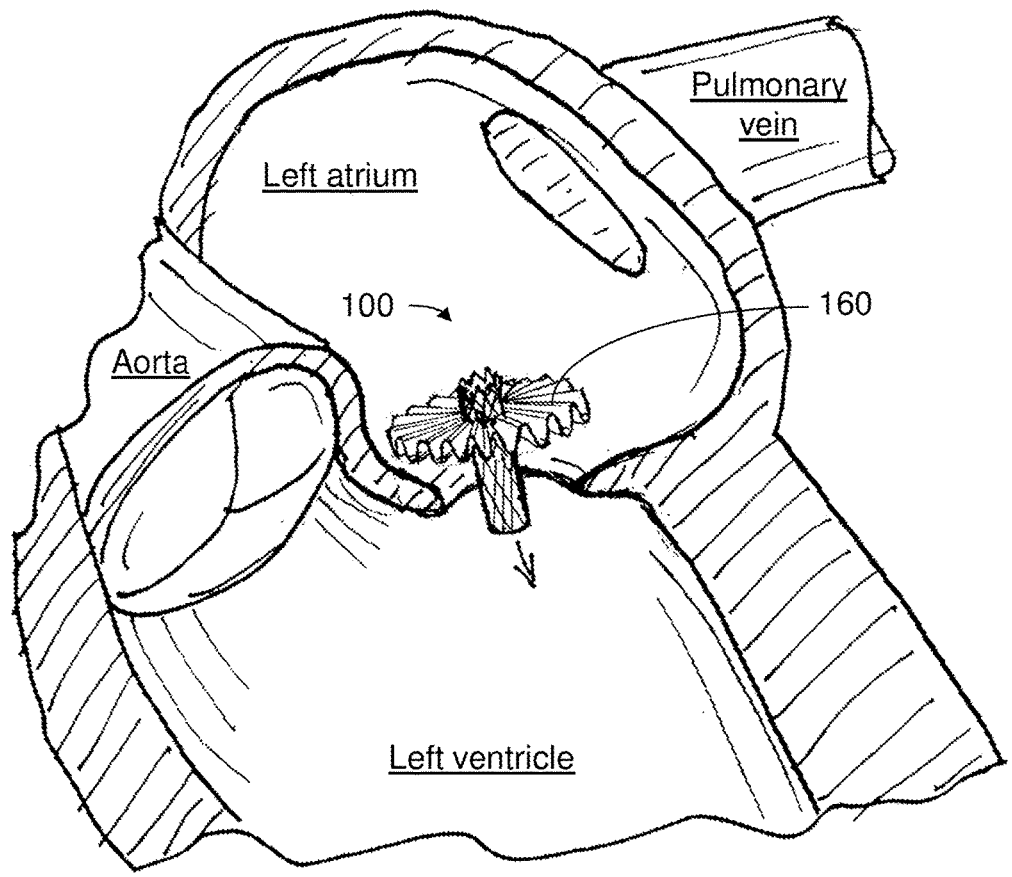
FIGS. 4A-4B depict deployment of an implantable device within a heart in accordance with some embodiments.
Figure 4B:
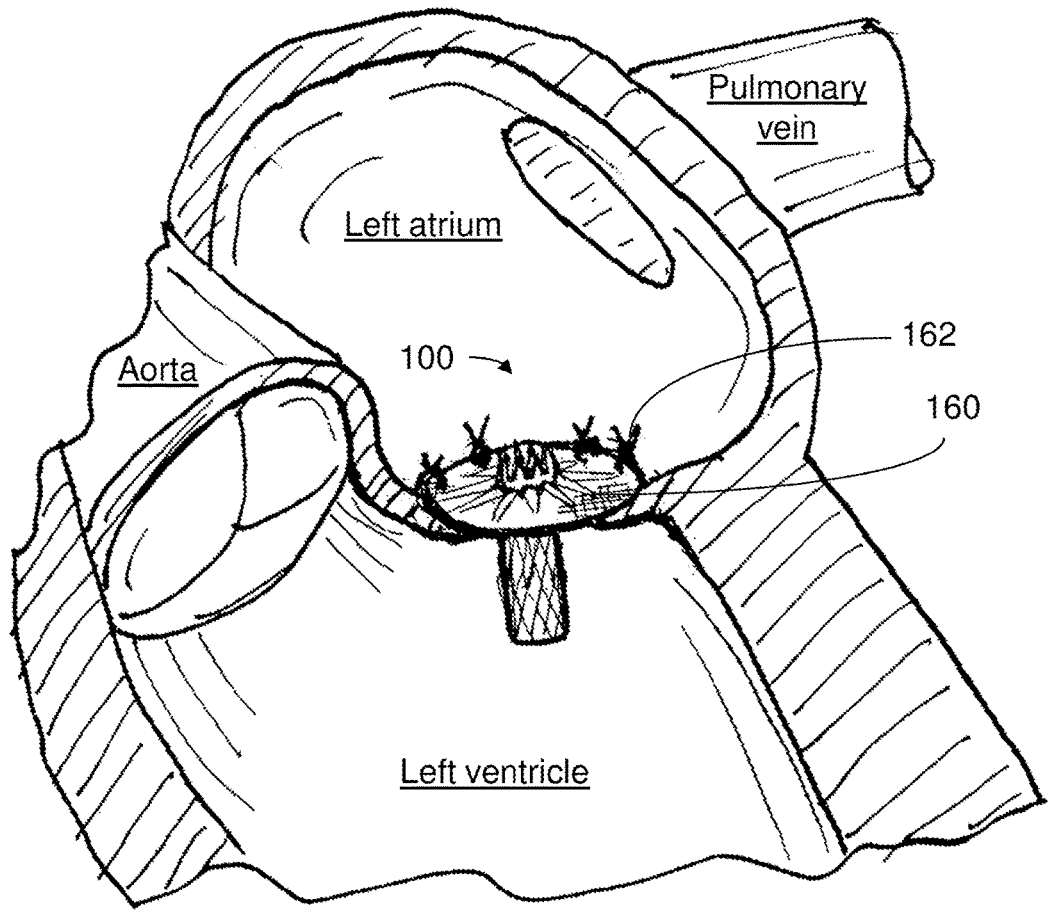

FIGS. 4A-4B depict an illustrative embodiment where the expandable stent valve device is implanted. Here, the device is surgically implanted (e.g., through open-heart surgery) into the annulus of tissue at the mitral valve position of the heart. As the device is positioned at the mitral valve position of the heart, a sewing member (shown here as a sewing cuff), which surrounds the valve frame at a region between the upstream end and the downstream end, is attached to the surrounding tissue. As discussed above, the sewing member 160 may be sutured or otherwise fixed (e.g., adhered, fastened, etc.) to the surrounding tissue.

The sewing member is also subsequently expandable, along with other components of the device. For example, and as shown in FIG. 4A, the sewing member 160 may be corrugated, pleated or otherwise constructed so as to accommodate expansion of the overall device while in a deployed state. In some cases, prior to expansion, the sewing member is constructed such that the device may be attached or otherwise fixed to the surrounding tissue, while not interfering with valvular fluid flow through the device. For example, the sewing member may have overlapping folds that allow sutures to be run through the folds of the sewing member during implantation and prior to expansion. When in a non-expanded state, corrugated features are compactly compressed together. When the device is expanded or otherwise dilated, the folds may separate from one another, while maintaining fixed attachment to the heart. In some embodiments, the sewing member may exhibit elastic characteristics, similar to a rubber band, so as to accommodate expansion of the device.

FIG. 4B illustrates the device 100 in a deployed state within the heart at the mitral valve position. As shown, the device is attached by the sewing member 160 to the tissue wall via sutured attachment points 162. Here, the device is in a deployed, yet pre-expanded state where the lumen of the valve frame has a relatively small diameter and other components (e.g., valve, sewing member, membrane) remain in a temporarily compressed state.

The expandable stent valve device may be attached or fixed to the surrounding tissue in any appropriate manner. In some embodiments, the sewing member surrounding the valve frame and valves is sutured to the appropriate surrounding tissue. For example, standard suture materials may pierce through the body of the sewing member and appropriate tissue incisions may be made, allowing the device and the tissue to be sutured together. In some embodiments, the body of the expandable valve frame may include suture holes where suture material may be threaded so that the valve frame and the tissue may be directly sutured together. Though, it can be appreciated that any suitable attachment technique may be used to join the device and the surrounding tissue, as sutures are not a required aspect of the present disclosure.

In some embodiments, the valve frame may be covered with a material (e.g., membrane covering) that can be attached or fixed to the surrounding tissue. In some embodiments, aspects of the valve frame, membrane and/or other component of the device promote tissue ingrowth such that the surrounding tissue provides for a biological attachment of the frame upon deployment. For example, the valve frame, membrane and/or other component may include a coating or a copolymer having an appropriate biomolecular arrangement that encourages tissue growth around the expandable valve frame. In some embodiments, portions of the expandable valve frame may be attached to surrounding tissue of the heart through a variety of other methods, such as through tissue welding (e.g., using laser and/or heat treatment), surgical staples, surgical adhesives (e.g., glue), and/or combinations thereof.

It should be appreciated that aspects of the present disclosure are not limited to the particular location where embodiments of the device may be implanted. For example, devices described herein may be deployed at any suitable location of the heart (e.g., mitral valve position, tricuspid position, semilunar position, ventricular outflow tracts, etc.) as well as other parts of the body, such as within or around conduits through which blood and/or other bodily fluids may flow. Embodiments of devices according to the present disclosure may also be used to suitably replace such bodily conduits as well.

Figure 5:
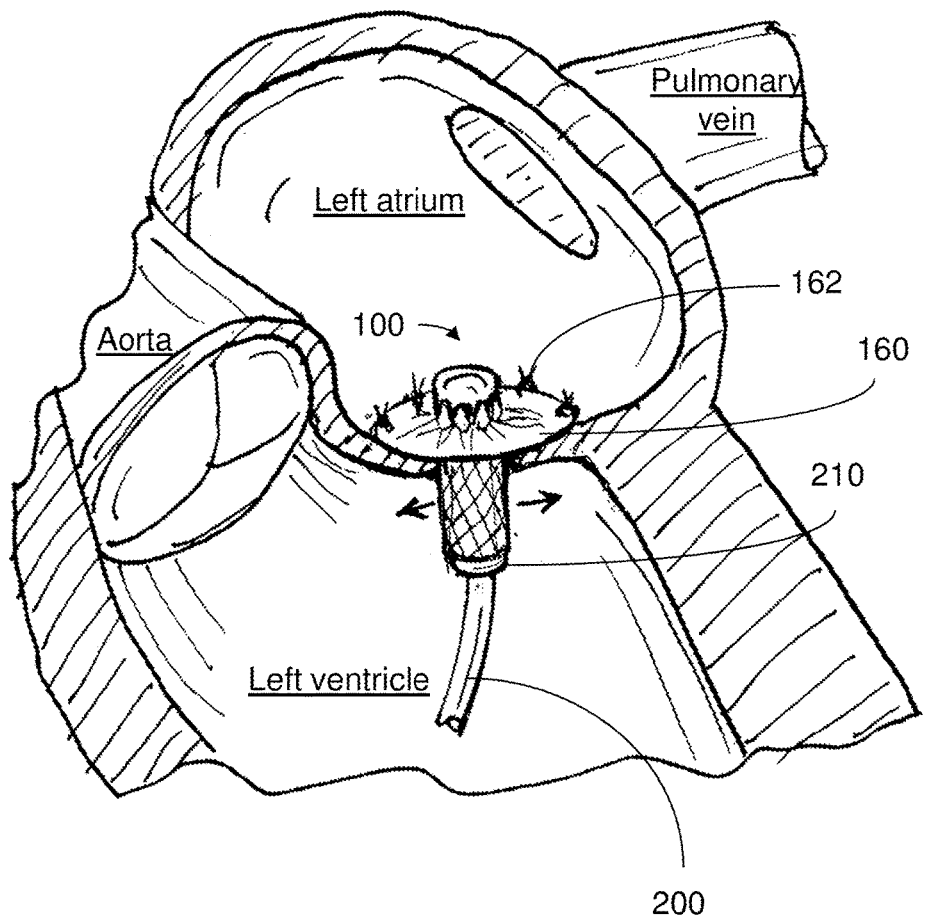
FIG. 5 shows expansion of the deployed implantable device of FIGS. 4A-4B in accordance with some embodiments.

As described herein, the device may be expanded during the implantation surgery or expanded at a later time, for example, so as to allow for growth in young patients. The device may be expanded to exhibit a larger diameter, for example, via transcatheter methods, as illustratively shown in FIG. 5. Here, a catheter 200 mounted with a transcatheter balloon 210 is guided through a series of blood vessels toward the heart and through a small aperture created through the septum of the heart (aperture not shown in the figures). After being directed through the aperture, the catheter travels through the internal chamber of the left ventricle and enters into the lumen of the device (e.g., through the downstream end). Once suitably situated within the lumen of the device, the transcatheter balloon 210 is inflated so as to apply an outward radial force upon the internal surface of the valve frame.

Upon suitable inflation of the balloon, the valve frame, along with other associated components of the device, is appropriately expanded. In some embodiments, the pressure applied by a balloon during expansion may be between about 2 atm and about 30 atm (in one embodiment, between about 2 atm and about 15 atm or, in another embodiment, between about 8 atm and about 30 atm). It can be appreciated that the valve frame 150 may be expanded using other techniques.

In some embodiments, the expandable valve frame may include a ratchet mechanism configured to maintain the size of the valve frame at particular stages, based on the amount of outward radial force applied. Accordingly, known and increasing amounts of force are required for increasing the diameter of the expandable valve frame, and/or other relevant components of the device, to successively larger diameters. In some embodiments, the diameter of the expandable valve frame is manually increased through appropriate tool manipulation. In some embodiments, the valve frame may have a series of discrete diameter settings that are reached based on how much force is applied to the frame, for controllability and to create a suitable fit for specific valve sizes within a given patient.

As discussed, suitable expandable valve frames described herein may have any suitable diameter D. As determined herein and shown in FIGS. 2C-2D, the diameter D of the valve frame is measured as the diameter of the lumen, which is the space provided between inner surfaces of the valve frame. In various embodiments, for an unexpanded configuration (e.g., initial configuration prior to expansion before or after implantation), the expandable valve frame may have a diameter of between about 1 mm and about 25 mm. For example, in an unexpanded configuration, the expandable valve frame may have a diameter of between 1 mm and 15 mm; between 1 mm and 10 mm; between 3 mm and 7 mm (e.g., 5 mm, 6 mm); between 5 mm and 15 mm; between 5 mm and 20 mm; between 7 mm and 25 mm; between 9 mm and 18 mm (e.g., 9 mm, 10 mm); between 10 mm and 20 mm; between 10 and 15 mm (e.g., 11-13 mm); between 10 mm and 25 mm; and/or between 15 mm and 25 mm.

In an expanded configuration (partially or fully expanded), in some embodiments, the expandable valve frame may have a diameter of between 1 mm and 30 mm. For example, in a partially or fully expanded configuration, the expandable valve frame may have a diameter of between 1 mm and 15 mm; between 1 mm and 10 mm; between 3 mm and 7 mm; between 15 mm and 30 mm; between 20 mm and 30 mm; between 25 mm and 30 mm; between 10 mm and 20 mm; between 10 and 15 mm (e.g., 13-15 mm); between 10 mm and 25 mm; and/or between 10 mm and 22 mm. As discussed above, in a suitably expanded, or pre-expanded configuration, the device maintains its valve function. That is, the device may be enlarged as appropriately desired without sacrificing valve function.

The device may be expanded to any suitable diameter between the initial and final diameters depending on patient growth and/or other factors. For example, the initial diameter of the device may be approximately 12 mm when implanted within a small baby. After a period of growth, for example, 1-2 years, the device may be expanded (e.g., through transcatheter methods) to approximately 14 mm.

Additionally, the device itself may be lengthened, or shortened, from an initial length to a final length. Accordingly, the valve frame may be structured such that, upon expansion of the diameter, the length of the valve frame increases or decreases. For example, when the valve frame is expanded, struts of the frame may be connected to one another in such a pattern where the distance between struts increases upon expansion, or vice versa. In various embodiments, an initial length of the valve frame may be about 1-30 mm (e.g., 5 mm) and a final length of the device may be about 10-20 mm (e.g., 15 mm). The implantable device may be suitably dimensioned based on the size of the patient. Accordingly, a device may be longer and have a larger diameter for implantation in older children as compared to a device for implantation in infants, where a shorter and narrower device may be appropriate.

Figure 6:
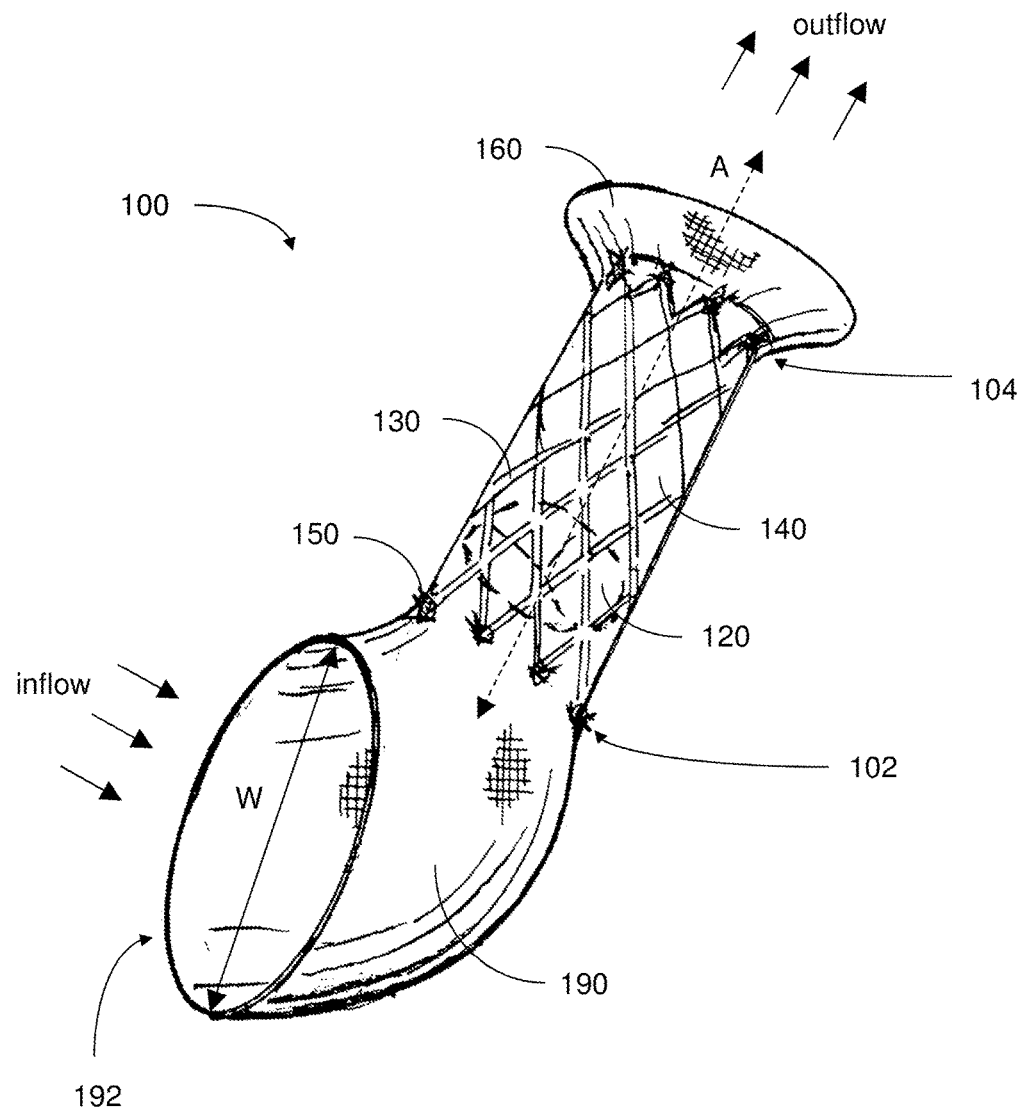
FIG. 6 illustrates a perspective view of another implantable device in accordance with some embodiments.

FIG. 6 depicts another illustrative embodiment of an expandable stent valve device 100. In some embodiments, the device shown in FIG. 6 may be suitable for implantation and deployment at a ventricular outflow tract (e.g., right ventricular outflow tract connecting the right ventricle to the pulmonary artery), although it can be appreciated that such a device may be deployed at other regions of the body.

The device 100 includes an optional valve 120 disposed within and attached to a valve frame 130. The valve frame 100 has an upstream end 102 (proximal end) through which fluid flows into the lumen defined by the valve frame, and a downstream end 104 (distal end) through which fluid flows out of the lumen defined by the valve frame, located opposite one another. Though, the upstream end of the device may be defined by an opening 192 of a covering 190, through which fluid may enter into the device, as depicted by three solid arrows labeled "inflow." The downstream end of the device may be located at the opposite end of the device and may be defined by the downstream end 104 of the valve frame, or a flared sewing member 160 (shown in FIG. 6), through which fluid flows out from the device, as depicted by three solid arrows labeled "outflow."

In accordance with aspects of the present disclosure, both the valve 120 and the valve frame 130 may be expandable upon application of a suitable amount of force. Components attached to the upstream end 102 (sewing member 160) and downstream end 104 (covering 190) are also suitably expandable.

The device may optionally include a membrane 140 attached and/or integrated along with the valve frame 130 so as to appropriately guide fluid flow through the lumen. The membrane, while not necessary, may serve to block leakage from the device by obstructing fluid flow between the lumen and the exterior of the device.

As further shown in FIG. 6, the device may include a covering 190 having a hood-like shape, with a relatively large opening 192 for receiving an inflow of fluid. The opening 192 may have a width W sufficiently wide to receive a substantial amount of fluid flow. In some embodiments, the width W of the opening is comparable to, or larger than, the diameter D of the lumen.

The covering, and its associated opening, may be adjusted and/or trimmed to have any appropriate shape for receiving and guiding fluid into the device. For example, the covering may be sized to fit snugly within the region defined by the right ventricular outflow tract. Accordingly, the opening of the covering may, in turn, have a suitable shape and be aligned to efficiently receive as much blood flow possible from the right ventricle. Though, it can be appreciated that aspects of the present disclosure are not limited to implantation at the right ventricular outflow tract, as the opening may be sized and shaped to receive fluid at any suitable location within the body.

Upon implantation of the device, the opening 192 is suitably arranged and positioned so as to receive fluid flowing near the upstream end 102 of the valve frame external to the device, and guide the flow into the lumen. For example, the opening 192 of the covering 190 may serve as an entrance to receive fluid flowing in a direction substantially perpendicular to the longitudinal axis A proximate the upstream end 102 of the valve frame, such as that shown by the three solid arrows of FIG. 6, depicting fluid inflow. That is, the opening 192 of the covering 190 serves as the upstream end of the device itself. The opening 192 of the covering 190 may be adapted, upon implantation, to face in a direction that is substantially perpendicular to the longitudinal axis A of the valve frame. On the other hand, the upstream end 102 of the valve frame 130 may have an opening that faces in a direction that is substantially parallel to the longitudinal axis A of the valve frame.

Accordingly, when suitably implanted, for example, at the right ventricular outflow tract, the opening of the covering may receive fluid flow from the right ventricle and direct such flow through the lumen of the valve frame and toward the pulmonary artery.

It can be appreciated that the device may exhibit a curvature, so as to suitably conform to the surrounding tissue structure. For example, the device may extend through portions of the right ventricular outflow tract and the pulmonary artery, which may each exhibit curvatures that vary with respect to one another. Accordingly, in some cases, the valve frame may define a passageway that bends or meanders from the longitudinal axis A, based on the anatomical curvature where the device is implanted.

In some embodiments, the downstream end of the device may be associated with a flared opening. Such a flared opening may accommodate attachment of the device to surrounding tissue. For example, the flared structure may provide space for the downstream end 104 of the valve frame to be attached to an appropriate region of the heart (e.g., right ventricular outflow tract, pulmonary artery). In various embodiments, the valve frame itself may be flared at the downstream end 104, or an additional component, such as a flared sewing cuff, such as that depicted in FIGS. 6-7, may be provided at the downstream end of the device which is, in turn, attached to the downstream end of the valve frame.

FIG. 6 depicts a sewing member 160 attached to the downstream end 104 of the valve frame where the sewing member is flared in the direction of outward flow. Here, the sewing member 160 is sutured or otherwise attached to the downstream end 104 of the valve frame 130. The flared sewing member 160 may, in turn, be attached to a tissue wall of the heart (e.g., pulmonary artery), or other appropriate region of the body. Accordingly, the flared end of the sewing member 160 may serve as the downstream end of the device itself.

Figure 7:
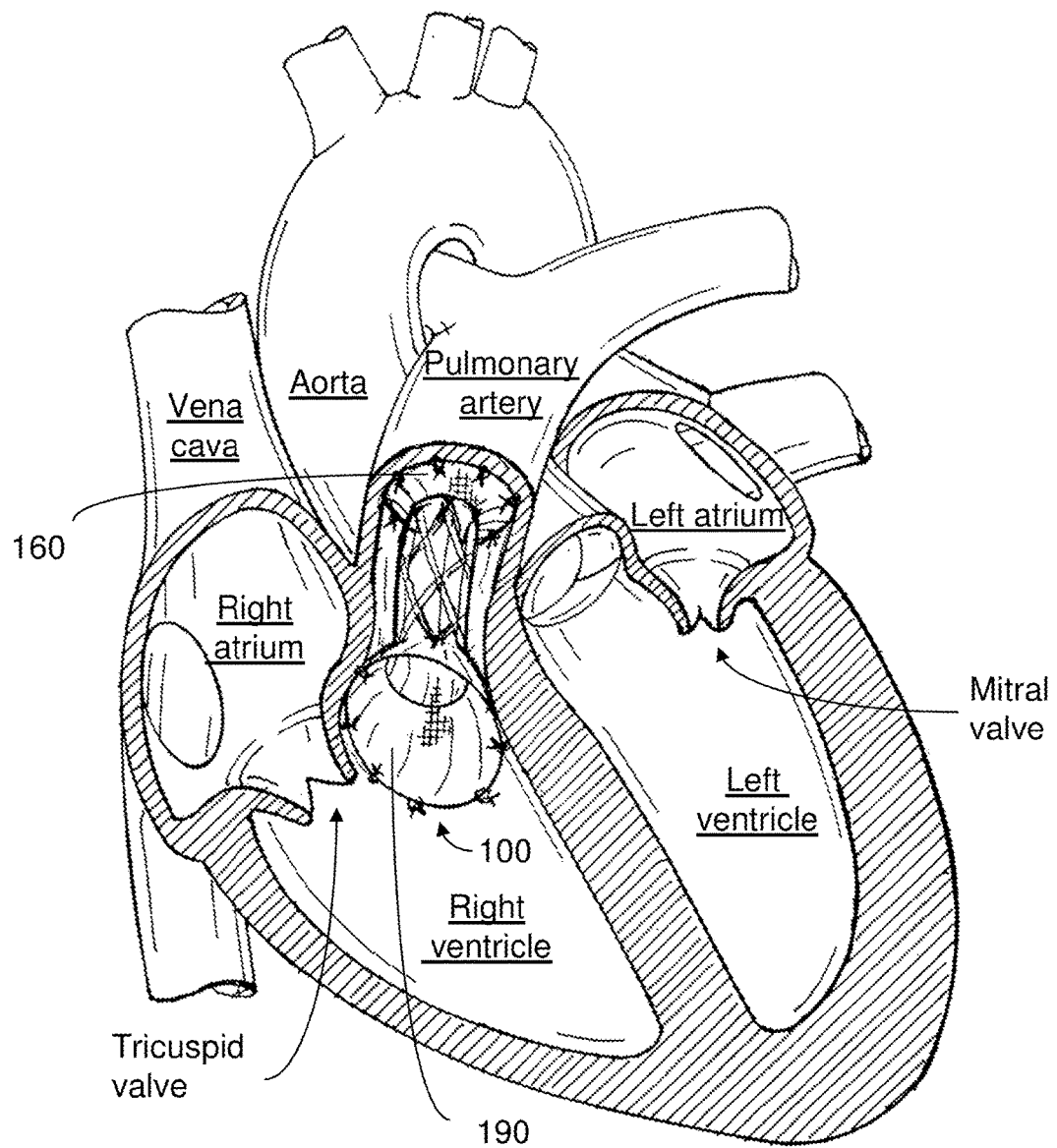
FIG. 7 shows an implantable device deployed within a heart in accordance with some embodiments.

FIG. 7 depicts an illustrative embodiment of an expandable stent valve device 100 implanted and deployed so as to replace the pulmonary valve, while also connecting the right ventricular outflow tract and the pulmonary artery. Here, opposite ends of the device are attached to the surrounding tissue. The covering 190 is attached to the wall of the right ventricle at the right ventricular outflow tract, on a side opposite the tricuspid valve. For example, as shown, the covering, which forms the upstream end of the device, is sutured along the periphery of the opening of the covering to incisions along the entrance of the right ventricular outflow tract such that the opening faces the majority of the chamber volume defined by the ventricle.

Anatomically, blood is pumped from the right atrium through the tricuspid valve into the right ventricle. Blood then flows from the right ventricle through the right ventricular outflow tract and into the pulmonary artery, toward the lungs. In some cases, the net direction in which blood flows into the right ventricle from the tricuspid valve may generally be substantially perpendicular to the orifice at the entrance of the right ventricular outflow tract. Accordingly, flow into the right ventricular outflow tract is often received at an angle substantially perpendicular to the net direction of flow through the outflow tract and toward the pulmonary artery.

The overall device structure may be based on the above anatomy. For example, upon implantation, the shape of the covering gives rise to a substantially bent flow path such that the opening of the covering is able to readily receive fluid flowing from the right ventricle. The covering and valve frame are then able to guide the fluid in a smooth manner (e.g., exhibiting a relatively laminar flow profile) toward and through the pulmonary artery. In some cases, if the covering is not appropriately bent or otherwise shaped so that the opening faces largely toward the main ventricle chamber, then flow through the device may be more turbulent than desired. Accordingly, it may be preferable for the opening of the covering to face in a direction that is substantially perpendicular (or angled within an appropriate range) with respect to the net direction of fluid flow through the valve frame and toward the pulmonary artery.

As shown in FIG. 7, the covering receives fluid flow through its opening from the right ventricle and directs the flow in a smooth, non-turbulent manner through the lumen of the valve frame and toward the pulmonary artery. Without such a covering, more effort may be required from the cardiac muscle than is desirable to force blood from the main chamber of the right ventricle and through the right ventricular outflow tract. In general, smooth, laminar flow from the right ventricle to the pulmonary article gives rise to greater pumping efficiency in the heart.

Downstream of the covering, the device has a flared opening that allows the device to be suitably attached to the surrounding tissue wall. FIG. 7 illustrates the device to have a flared sewing cuff 160 extending from the downstream end of the valve frame. The pulmonary artery provides a relatively small space within which a medical device may be implanted, thus, the flared structure of the sewing cuff provides slack with which a surgeon may attach the device, via the sewing cuff, to the wall of the pulmonary artery. It can be appreciated that any appropriate technique may be used to attach the flared portion of the downstream end of the device to the surrounding tissue. As shown, an upstream portion of the sewing cuff 160 is attached to the downstream end 104 of the valve frame. The flared downstream portion of the sewing cuff is, in turn, sutured or otherwise attached to the tissue wall of the heart.

In this embodiment, the device 100 is implanted via suture attachments at the covering 190, located at the upstream end of the device, and the sewing cuff 160, located at the downstream end of the device. Thus, the device provides a passageway for blood flow between the right ventricle and the main pulmonary artery, through the valve 120.

Such a passageway that the device provides may have a suitable length, for example, between 1.0 cm and 3.0 cm, between 1.0 cm and 2.0 cm, between 1.5 cm and 2.0 cm, or another suitable distance.

As noted herein with respect to each of the components of the expandable stent valve device 100, the hood-like covering 190 and flared sewing cuff 160 are also made up of material that is expandable along with the valve frame and valve disposed therein.

In some embodiments, upon implantation, the properties of tissue regions where respective upstream and downstream ends of the device (e.g., covering and sewing cuff) are sutured or otherwise attached may differ. That is, the properties of the tissue at a right ventricle wall to which the covering may be attached may differ substantially from the properties of the tissue at a wall of a pulmonary artery to which the downstream (flared) sewing cuff, or (flared) downstream end of the valve frame, may be attached. For example, an expandable membrane or sewing cuff attached at an arterial outlet may be thicker than an expandable membrane or sewing cuff attached at a venous outlet, or vice versa. In such a case, the expandable membrane or cuff having a larger thickness may be able to provide added support for accommodating increased fluid pressure at an arterial location in comparison to a venous location, or vice versa.

It can be appreciated that embodiments of the present disclosure may be used to treat a variety of conditions other than those specifically discussed above. For example, devices described herein may be implanted within the body of a patient suffering from a single ventricle defect, where the heart only has a single adequately functioning pumping chamber, or ventricle (e.g., existing chamber may be too small, chamber may be underdeveloped, a valve may be missing, occurrence of atresia, etc.).

In some embodiments, the device may be incorporated in a transmural implantation that extends from a ventricular cavity (e.g., right ventricle, left ventricle, single ventricle) across the ventricular wall and connects to a vessel (e.g., pulmonary artery, aorta) on the opposite side. For example, the valve frame, with an optional valve located therein, may be interposed between a proximal segment (e.g., tube graft), that connects to the ventricle, and a distal segment (e.g., tube graft), that connects to a bodily vessel. That is, the surgically implanted device may include the valve and valve frame with tubular grafts connected to the valve frame on opposite sides. The grafts, in turn, form connections with the ventricle and the vessel so that blood is able to flow from the ventricle through the valve frame to the vessel.

Though, for some embodiments, a single tubular graft may be employed on one side of the valve frame. For example, the valve frame may be directly attached to the blood vessel (e.g., pulmonary artery) and a tube graft may extend from the valve frame to the ventricle, or vice versa, where the valve frame may be directly attached to the ventricle and a tube graft may extend from the valve frame to the blood vessel.

The proximal (or upstream) portion of the surgically implanted device may be structurally reinforced, including stiffer and/or more material (e.g., structurally reinforced polymers, metal, composite materials, etc.) placed external and/or internal to the device, so as to resist collapse of the portion of the device that extends across the ventricular wall. For instance, a tube graft that extends from the valve frame and across the ventricular wall may incorporate such structural reinforcements, particularly at the location where the tube extends across the tissue wall.

As an example, a device having a valve frame, with a valve included therein, and tubular grafts connected on opposite sides of the valve frame may be transmurally implanted so as to extend from the right ventricle to the pulmonary artery. The proximal tubular segment may be structurally reinforced and attached to the ventricle in a position such that the segment suitably lies across the ventricular wall, for fluid/blood to flow from the ventricle through the tube. The distal tubular segment may be suitably connected to the pulmonary artery, for example, grafted to the pulmonary artery via a tube graft (e.g., PTFE tube), or other appropriate material. As a result, blood may flow from the right ventricle through the proximal graft segment, through the valve within the valve frame, through the distal graft segment, and into the pulmonary artery.

As discussed above, the device may or may not include a valve, for example, located along the mid-section of the tube. As the device may extend outside of the heart, or portions thereof, during a transmural implantation, more space may be provided for the device to include a valve than would otherwise be the case if the device is implanted within a more restricted region of the heart (e.g., at a mitral or tricuspid position). In some embodiments, the diameter of the valve may be between 1 mm and 15 mm, between 1 mm and 10 mm, between 2 mm and 8 mm, or between 3 mm and 7 mm (e.g., approximately 5-6 mm).

Similar to other embodiments described herein, the valve and/or valve frame of the device may also be expandable, as desired, to accommodate growth or other physical requirements of the patient's anatomy.

In addition, the tube grafts may be made up of any suitable material. For example, the tube grafts may be biological (e.g., bovine, human, porcine, allograft, xenograft, etc.) and/or synthetic (e.g., polymeric, PTFE, composite, metal, etc.) in nature.

As discussed above, the passageway defined by the device may be straight or curved in configuration, so as to accommodate the anatomical structure to which the device is implanted. In another aspect of the present disclosure, the overall curvature of the valve frame, or other portion(s) of the device may be adjusted.

In some cases, before or after implantation, the valve frame may be shaped by a suitable curved template, dilator, or other structure to exhibit a desired curvature. Such a template may provide the device with one or more curvatures, i.e., the device may exhibit, along its length, more than one radius of curvature.

As discussed above, it may be desirable for the valve frame, or other portion(s) of the device, to conform as much as possible to the anatomical structure within which it is implanted. Such an anatomical structure may include a tract or vessel that exhibits multiple degrees of curvature. For example, an outflow tract (e.g., RVOT), or associated vessel, may define a pathways having only a slight degree of initial curvature and, further along the tract (e.g., branch of a pulmonary artery), the pathway may exhibit a greater degree of curvature. Accordingly, upon implantation and subsequent expansion, the device may have a shape that complements the surrounding anatomy, i.e., exhibit multiple degrees of curvature at various locations.

In some embodiments, a curved mandrel or dilator may be used to shape (e.g., crimp) the valve frame before implantation. For instance, prior to implantation, a curved mandrel may be inserted through the lumen of the valve frame so as to pre-shape the device.

During an implantation operation, a surgeon may have access to a plurality of curved mandrels having different curvatures, shapes and sizes from which to select. For example, the radius of curvature for one mandrel may be significantly larger than the radius of curvature for another mandrel. Alternatively, a single mandrel may be provided where the curvature along the length of the mandrel may be adjusted according to the desired curvature(s) of the device. Or, in some cases, a mandrel may include an irregularly or an elliptically-shaped arc. Hence, a surgeon may inspect the anatomy of the patient and adjust the device (e.g., crimping about a suitably shaped mandrel) to incorporate the type of curvature that is most appropriate, upon implantation. When the device is suitably deployed, the valve frame, or other portion(s) of the device, conforms to the curvature of the surrounding tissue where the device is located.

Or, a balloon having pre-shaped curvature may be inserted through the lumen of the valve frame and expanded. For example, the balloon may be deployed through transcatheter methods and, upon expansion, may exhibit the pre-shaped curvature(s) upon expansion. As discussed above, the balloon may exhibit a slight degree of curvature at one region and a sharper degree of curvature at another region. As the balloon applies an outward radial pressure, the valve frame then conforms to the balloon curvature(s).

In some embodiments, and as discussed, the balloon, when expanded, may be elongated and may further exhibit multiple degrees of curvature along its length. For example, upon inflation of an elongated balloon used to expand devices according to the present disclosure, various regions of an elongated balloon may have radii of curvature that are different from one another.

Over time and use, an implanted valve may deteriorate to a point of malfunction (e.g., through disease, damage, and/or age). That is, upon malfunction, the implanted valve is unable to properly control flow unidirectionally away from one chamber or passageway to another or may become obstructed due to tissue ingrowth. In some cases, portions of the implanted valve are resorbed over time, for example, through exposure to bodily fluids (e.g., blood). In other cases, portions of the implanted valve are left open or possibly torn. Inability for the implanted valve to properly function may include leakage through portions of the valve or obstruction through the lumen of the valve frame.

Embodiments of expandable stent valve devices described herein may be implanted at a location within the body where a previous replacement valve had been implanted. That is, a subsequent stent valve device may replace the function of the first valve device, for example, by supporting the previously implanted valve or replacing the previous valve entirely. Accordingly, the valve frame may function as an implant site, or docking station, for future valve replacements (e.g., through surgical and/or transcatheter methods), allowing for one or more valves to be implanted sequentially.

An additional expandable stent valve device may be attached to the previous valve device by any suitable method, for example, through an interlocking attachment mechanism, suturing, etc. In some cases, the subsequent expandable stent valve device is pushed up against the inner wall of the bodily vessel in a manner that the device remains stably situated. For instance, a balloon may be used to provide an outward force to the additional valve device so as to anchor the additional valve device to the previously implanted device as well as the surrounding vessel tissue.

Embodiments described may be for use as an improvement of the Melody Transcatheter Pulmonary Valve, manufactured by Medtronic, Inc. However, it should be appreciated that aspects of the invention may be used in any suitable arrangement where a valve conduit is incorporated. Also, valve conduits described may be used to provide a fluid passageway between any appropriate regions, such as for example, between ends of a resected bodily vessel, cavities and/or channels within the body.

The above aspects may be employed in any suitable combination as the present invention is not limited in this respect. Also, any or all of the above aspects may be employed in a valve arrangement; however, the present invention is not limited in this respect, as aspects of the may be employed with other medical devices.

Having thus described several aspects of at least one embodiment of this invention, it is to be appreciated various alterations, modifications, and improvements will readily occur to those skilled in the art. For example, the prosthesis described herein may be adapted for placement in other locations. In some embodiments, prosthesis described herein may include material that is radioopaque so that suitable imaging may occur. Such alterations, modification, and improvements are intended to be part of this disclosure, and are intended to be within the spirit and scope of the invention. Accordingly, the foregoing description and drawings are by way of example only.

What is claimed is:

1. A device for implantation at a position of a heart, the device comprising:
   a valve frame defining a lumen, the valve frame having an upstream end and a downstream end;
   a plurality of valve leaflets attached to and disposed within the valve frame;
   a sewing member surrounding the valve frame at a region between the upstream end and the downstream end, for forming an attachment to tissue at the position of the heart; and
   a membrane disposed about the valve frame for obstructing fluid flow between the lumen and an external region surrounding the valve frame,
   wherein the valve frame is expandable, and a portion of the membrane at a side region of the downstream end of the valve frame comprises an opening that permits fluid flow through the side region.

2. The device of claim 1, wherein the valve frame is expandable from a first diameter between 9 mm and 18 mm to a second diameter between 10 mm and 22 mm.

3. The device of claim 1, wherein the sewing member is expandable.

4. The device of claim 1, wherein the sewing member is attached to the valve frame.

5. The device of claim 1, wherein the opening comprises a cut out of the membrane extending along a plane that is parallel to or forms an angle with respect to a longitudinal axis of the valve frame.

6. The device of claim 5, wherein a downstream end of the membrane comprises a cut out extending along a plane that is substantially perpendicular to the longitudinal axis of the valve frame.

7. The device of claim 1, wherein the sewing member comprises a corrugated cuff.

8. The device of claim 1, wherein the valve frame is expandable from a first diameter between 11 mm and 13 mm to a second diameter between 13 mm and 15 mm.

9. The device of claim 1, wherein an edge of at least one of the upstream end and the downstream end of the valve frame has a level surface.

10. The device of claim 1, further comprising an attachment region proximate to the downstream end of the valve frame, for forming an attachment to tissue at a wall of the heart.

11. The device of claim 1, wherein the valve frame has a length of between 1.0 cm and 2.5 cm.

12. The device of claim 1, wherein the sewing member is located substantially concentric with the plurality of valve leaflets.

13. The device of claim 1, wherein the position comprises a mitral valve position of the heart.

14. The device of claim 1, wherein the sewing member surrounds the valve frame at approximately a midpoint between the upstream end and the downstream end.

15. A method of implanting a device at a position of the heart, the device including a valve frame defining a lumen, the valve frame having an upstream end and a downstream end, a plurality of valve leaflets attached to and disposed within the valve frame, and a membrane disposed about the valve frame for obstructing fluid flow between the lumen and an external region surrounding the valve frame, wherein the valve frame is expandable, and a portion of the membrane at a side region of the downstream end of the valve frame comprises an opening that permits fluid flow through the side region, the method comprising:
   positioning the valve frame at the position of the heart; and
   attaching a sewing member surrounding the valve frame at a region between the upstream end and the downstream end to tissue at the position of the heart.

* * * * *